United States Patent [19]

Lin et al.

[11] 4,250,122

[45] Feb. 10, 1981

[54] PROCESS AND CATALYST MIXTURE FOR THE PARA-DIRECTED CHLORINATION OF ALKYLBENZENES

[75] Inventors: Henry C. Lin, Grand Island; Stephen Robota, North Tonawanda, both of N.Y.

[73] Assignee: Hooker Chemicals & Plastics Corp., Niagara Falls, N.Y.

[21] Appl. No.: 73,472

[22] Filed: Sep. 7, 1979

Related U.S. Application Data

[63] Continuation of Ser. No. 874,968, Feb. 3, 1978, abandoned.

[51] Int. Cl.$^3$ .............................................. C07C 25/06
[52] U.S. Cl. ...................................... 570/209; 570/210
[58] Field of Search ..................................... 260/650 R

[56] References Cited

U.S. PATENT DOCUMENTS 3,217,044  11/1965  Klug et al. ............................ 260/609
4,069,263  1/1978   Lin ...................................... 260/650 R

FOREIGN PATENT DOCUMENTS 1123663  2/1962  Fed. Rep. of Germany .
1222508  8/1966  Fed. Rep. of Germany .
1116353  6/1968  United Kingdom .

Primary Examiner—Curtis R. Davis
Attorney, Agent, or Firm—Peter F. Casella; William J. Crossetta, Jr.; Arthur S. Cookfair

[57] ABSTRACT

A process for the para-directed chlorination of alkylbenzenes comprises reacting an alkylbenzene with chlorine in the presence of a catalyst mixture previously prepared by the steps of (a) reacting sulfur monochloride with toluene or chlorotoluene in the presence of a Lewis acid catalyst, and (b) reacting the reaction product of step (a) with chlorine.

11 Claims, No Drawings

PROCESS AND CATALYST MIXTURE FOR THE PARA-DIRECTED CHLORINATION OF ALKYLBENZENES

This is a continuation of application Ser. No. 874,968, filed Feb. 3, 1978, and now abandoned.

BACKGROUND OF THE INVENTION

This invention relates to a catalyst mixture useful as a paradirecting catalyst for the nuclear chlorination of alkylbenzenes.

The chlorination of alkylbenzenes such as toluene, to prepare nuclear-substituted chlor-alkylbenzenes, such as monochlorotoluene, is well known and of considerable commercial importance. Such reactions are generally carried out in the presence of a chlorination catalyst such as antimony chloride, ferric chloride, aluminum chloride, and the like. The usual products of such reactions are a mixture of various monochlorinated and/or polychlorinated compounds and various positional isomers of these. For example, in the liquid phase substitution-chlorination of toluene, by reaction of chlorine and toluene, to form monochlorotoluene, the usual product is primarily a mixture of orthochlorotoluene and parachlorotoluene which may, in addition, contain varying amounts of other chlorinated products such as metachlorotoluene, dichlorotoluene, polychlorotoluenes and benzylic chlorides. Of the major reaction products, that is orthochlorotoluene and parachlorotoluene, the latter is the most commercially valuable. Because of the greater commercial value of parachlorotoluene, considerable effort has been expended in attempts to direct the chlorination reaction in such a manner as to lower the ratio of orthochlorotoluene to parachlorotoluene, that is, to discover reaction conditions under which the formation of parachlorotoluene is favored.

It is known from U.S. Pat. No. 1,946,040 that when alkylbenzenes are reacted with chlorine, the yield of parachlorinated product is improved with the aid of a mixed catalyst comprising sulfur and antimony trichloride and, optionally, iron or lead.

In British Pat. No. 1,153,746(1969) it is disclosed that in the chlorination of toluene in the presence of a ring chlorination catalyst, such as ferric chloride, antimony chloride, and the like, the ratio of orthochloro to para-chloro isomers produced may be lowered by the presence of an organic sulfur compound such as thiophene, hexadecylmercaptan, dibenzothiophene or the like.

British Pat. No. 1,163,927(1969) discloses that the formation of parachlorotoluene is enhanced when toluene is reacted with chlorine in the presence of elemental sulfur, or an inorganic sulfur compound, and a ring chlorination catalyst, such as ferric chloride, aluminum chloride, antimony chloride, zinc chloride, iodine, molybdenum chloride, stannous chloride, zirconium chloride, or boron trifluoride.

U.S. Pat. No. 3,226,447(1965) teaches that in the substitution-chlorination of benzene and toluene, the ratio of ortho isomer to paraisomer in the mono-chlorinated product may be lowered when the reaction is carried out in the presence of an iron, aluminum or antimony halide catalyst and a co-catalyst which is an organic sulfur compound wherein the sulfur is divalent. Examples of such co-catalyst include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur.

According to U.S. Pat. No. 3,317,617(1967) the formation of parachlorotoluene is favored when toluene is reacted with chlorine in the presence of platinum dioxide.

U.S. Pat. No. 4,031,144(1977) discloses that a monochlorotoluene product having an unusually high parachlorotoluene content is obtained when toluene is chlorinated in the presence of a catalyst system that contains a ferrocene compound and a cocatalyst that is sulfur or a compound that contains at least one divalent sulfur atom, such as sulfur, sulfur monochloride, sulfur dichloride carbon disulfide, thiophenes, thiophanes, alkyl-, cycloalkyl-, aryl-, and aralkyl mercaptans and dimercaptans, thioethers, and the like.

U.S. Pat. No. 4,013,730(1977) discloses a process for the preparation of monochlorotoluene having a reduced orthochloro- to parachloroisomer content which comprises reacting toluene with chlorine in the presence of a catalyst system comprising a Lewis acid catalyst and, as a co-catalyst, diphenyl selenide or aluminum selenide.

Still further improvements in the preparation of monochlorotoluene having a low ortho to para isomer ratio are disclosed in U.S. Pat. Nos. 4,031,142 and 4,031,147(1977). U.S. Pat. No. 4,031,142 discloses a process for the preparation of nuclear chlorinated alkylbenzenes, such as monochlorotoluene which comprises reacting an alkylbenzene, such as toluene, with chlorine in the presence of a Lewis acid catalyst and, as a cocatalyst, thianthrene. In accordance with U.S. Pat. No. 4,031,147, even lower ratios of ortho to para isomer are obtained in monochloroalkylbenzene products prepared by the reaction of an alkylbenzene with chlorine in the presence of a Lewis acid catalyst and a thianthrene compound having electron-withdrawing substituents, such as chlorine, present at the 2,3,7, and/or 8 position of the thianthrene nucleus.

U.S. Pat. Nos. 4,069,263 and 4,069,264 disclose processes for the directed nuclear chlorination of alkylbenzenes wherein an alkylbenzene, such as toluene is reacted with chlorine in the presence of a substituted thianthrene having both electron-withdrawing substituents and electron-donating substituents on the nucleus thereof.

Although various processes for the directed nuclear chlorination of alkylbenzenes are known in the art, it will be appreciated that advantages are to be derived from the development and use of para-directing catalysts that may be more simply and economically synthesized from readily available raw materials and which will effectively enhance the production of para-chloro isomers in the chloroalkylbenzene product.

It is an object of the present invention to provide an improved process for the directed nuclear chlorination of aromatic compounds. It is a further object to provide a process for the directed nuclear chlorination of alkylbenzenes, especially toluene, whereby the chlorinated product is characterized by a desirably low ratio of orthochloro to para-chloro isomers. It is a still further object to provide an improved para-directing nuclear chlorination catalyst mixture for such processes, that may be conveniently synthesized from readily available raw materials.

SUMMARY OF THE INVENTION

In accordance with this invention there is provided a process for the directed nuclear chlorination of alkylbenzenes which comprises reacting an alkylbenzene with chlorine in the presence of a catalyst mixture previously prepared by the steps of (a) reacting sulfur monochloride with toluene or chlorotoluene in the presence of a Lewis acid catalyst; and (b) reacting the reaction product of step (a) with chlorine.

The catalyst mixture of this invention, prepared by reaction of sulfur monochloride with toluene or monochlorotoluene in the presence of a Lewis acid catalyst and subsequent reaction with chlorine may be employed as a para-directing nuclear chlorination catalyst without additional purification or separation of components. Thus the present catalyst mixture and para-directed chlorination process provides a substantial advantage over the prior art para-directing chlorination catalysts and processes, in terms of simplicity of preparation and use of the catalyst mixture, while at the same time providing excellent catalytic activity in the nuclear chlorination of alkylbenzenes where a high percentage of parachlorobenzene product is desired.

DETAILED DESCRIPTION OF THE INVENTION

The catalyst mixture of this invention is preferably prepared by first slowly adding sulfur monochloride to a mixture of a Lewis acid catalyst and toluene or chlorotoluene and allowing the components to react. The temperature of the reaction mixture may vary considerably, for example, from temperatures as low as $-20°$ Celsius to the boiling point of the reaction. Preferably the temperature is maintained in the range of about 0° to about 80° Celsius and most preferably about 20° to about 60° Celsius. In the subsequent step in the preparation of the catalyst mixture, that is the chlorination of the reaction product of the first step, a similarly wide range of reaction temperatures may be employed. It is preferred, however, to carry out the chlorination of the reaction mixture at a somewhat higher temperature than that employed in the first step, and preferably in the range of about 40° to about 80° Celsius.

The proportions of reactants employed in the preparation of the catalyst mixture may vary considerably. It is preferred, however, that the first step in the catalyst mixture preparation be carried out utilizing a weight ratio of toluene or chlorotoluene: sulfur monochloride of between about 100:1 and about 0.1:1 and most preferably about 20:1 to about 5:1. It is further preferred to employ a weight ratio of sulfur monochloride: Lewis acid catalyst of about 50:1 to about 5:1.

The toluene or chlorotoluene component employed in the preparation of the catalyst mixture includes toluene, orthochlorotoluene, metachlorotoluene, parachlorotoluene, as well as the various dichloro-, trichloro- and tetrachlorotoluenes and isomers thereof. The preferred toluene or chlorotoluene component, based on economic factors as well as efficiency of the catalyst mixture is monochlorotoluene and most preferably orthochlorotoluene.

A wide variety of known Lewis acid catalysts may be employed in the preparation of the catalyst mixture. The term "Lewis acid catalyst" as employed herein includes, in addition to Lewis acids, those compounds or elements that will form or function as Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides, oxychlorides, oxides and elemental forms of antimony and iron. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like. The preferred Lewis acid catalyst is ferric chloride.

Following the reaction of toluene or chlorotoluene with sulfur monochloride in the presence of a Lewis acid catalyst the reaction product is reacted with chlorine, preferably by introducing chlorine gas into the liquid reaction product. It is preferred to dilute the reaction product of step (a) with additional toluenes or chlorotoluenes in amounts of about 25 to about 200 percent by weight based on the weight of reaction product of step (a), prior to the chlorination step (b). The amount of chlorine gas introduced into the diluted reaction medium may vary considerably, but will typically be in an amount of about 10 to about 100 parts of chlorine per 100 parts by weight of the reaction medium.

The catalyst mixture, thus prepared, may be employed without further treatment, as a para-directing nuclear chlorination catalyst in the chlorination of alkylbenzene compounds. The alkylbenzenes which may be chlorinated in accordance with this invention include the various monoalkyl-, dialkyl-, and polyalkyl-substituted benzenes wherein the alkyl group may be straight chain or branched, substituted or unsubstituted. The preferred alkylbenzenes are those wherein one or two alkyl group of 1 to 4 carbon atoms are present on the benzene nucleus, especially toluene and xylene. It will be appreciated that, although the preparation of monochloroalkylbenzenes, having a relatively high proportion of parachloroalkylbenzene, is an important object of the present invention. The monochloro product may be further chlorinated, if desired, to produce higher chlorinated derivatives.

The amount of catalyst mixture employed in the chlorination of alkylbenzenes, in accordance with this invention, may vary considerably, for example, in amounts of about 0.1 to about 10 percent and preferably about 0.5 to about 5.0 percent by weight of the catalyst mixture based on the weight of alkylbenzene reactant. The catalyst mixture may be employed alone or with an additional catalyst, especially a Lewis acid catalyst such as disclosed hereinabove. In one embodiment of this invention alkylbenzenes are reacted with chlorine in the presence of the catalyst mixture together with iron metal as a co-catalyst.

Under atmospheric pressure, the chlorination of alkylbenzenes, in accordance with the present invention, may be carried out over a wide range of temperatures, ranging for example from sub-zero temperatures such as $-30°$ Celsius or below to over 100° Celsius. The upper limit of temperature is, of course, determined by the boiling point of the reaction medium, and may, depending on the boiling point limitation, range as high as 150° Celsius or higher. However, no practical advantage is gained through the use of higher temperatures or extremely low temperatures, and it is preferred to utilize temperatures in the range of about −20° to about 110° Celsius, and most preferably in the range of about 0° to about 70° Celsius. The optimum temperature will vary somewhat, depending on the particular alkylbenzene and catalyst system employed.

Although it is preferred to carry out the process at atmospheric pressures, subatmospheric or superatmospheric pressures may be employed if desired.

In a preferred embodiment, this invention relates to a process for the chlorination of toluene in the presence of a catalyst mixture previously prepared by (a) reacting sulfur monochloride with orthochlorotoluene in the presence of a Lewis acid catalyst, preferably ferric chloride, and (b) reacting the reaction product of step (a) with chlorine. In the chlorination of toluene in this manner, monochlorotoluene products having a ratio of orthochlorotoluene: parachlorotoluene of less than about 1.0 are obtainable. In the chlorination of toluene, the desired monochlorotoluene product is generally parachlorotoluene, whereas orthochlorotoluene is generally an undesired by-product of considerably less commercial value. Thus, it is an unexpected advantage that a catalyst mixture utilizing orthochlorotoluene may be effectively employed in the aforesaid manner to lower the proportion of orthochlorotoluene produced during the chlorination of toluene.

The following specific examples are provided to further illustrate this invention and the manner to which it may be carried out. It will be understood, however, that the specific details given in the examples have been chosen for purpose of illustration and are not to be construed as a limitation of the invention. In the examples, unless otherwise indicated, all parts and percentages are by weight and all temperatures are in degrees Celsius.

EXAMPLE 1

A mixture of 253 parts of orthochlorotoluene and 19.5 parts of ferric chloride was charged to a reaction vessel and heated to about 50° C. The mixture was continuously stirred and maintained at about 50° C. while 27 parts of sulfur monochloride was added slowly over a period of about one half hour. Following the addition of sulfur monochloride, the reaction mixture was maintained at about 50° C., with stirring, for about three hours, then diluted with an additional 400 parts of orthochlorotoluene and heated to about 70° C. The mixture was maintained at about 70° C. with stirring, while 208 parts of chlorine gas was introduced slowly over a period of about 10 hours. The mixture was then allowed to cool to room temperature. The resultant reaction product comprises 634 parts of a dark green liquid suitable for use as a catalyst mixture for the para-directed chlorination of alkylbenzenes. Analysis of the reaction product by gas chromotographic method indicated a composition (in area %) of 74.28% dimethyldichlorothianthrene; 14.46% dimethyltrichlorothianthrene; 1.59% dimethyltetrachlorothianthrene; and 6.64% of unknown components.

EXAMPLES 2–5

Catalyst mixtures were prepared in a manner substantially as described in Example 1 except that the amount of reactants were varied as shown in Table I, below. Analysis of the reaction mixture by gas chromatographic techniques (area %) indicated the primary component in each instance to be dimethyldichlorothianthrene, with lesser amounts of various higher chlorinated dimethylthianthrene and unknown components.

TABLE I

| Ex. No. | Ortho-chloro-toluene* | $S_2Cl_2$* | $FeCl_3$* | Additional Orthochloro-toluene Diluent Added Prior to Chlorination* | Chlorine* | Yield of Catalyst Mixture* |
|---|---|---|---|---|---|---|
| 1 | 253 | 27 | 19.5 | 400 | 208 | 634 |
| 2 | 253 | 27 | 9.75 | 400 | 151 | 598 |
| 3 | 253 | 27 | 3.25 | 400 | 221 | 704 |
| 4 | 127 | 13.5 | 1.65 | 200 | 223 | 351 |
| 5 | 127 | 13.5 | 0.83 | 200 | 234 | 375 |

*parts by weight

EXAMPLE 6

A mixture of 100 parts of toluene and 2 parts of the catalyst mixture prepared as in Example 1 was heated and maintained at a temperature of 50° C., with stirring while 61 parts of chlorine gas was introduced into the reaction mixture over a period of 4.7 hours. The reaction mixture was then quenched with water, extracted with diethyl ether, and dried over anhydrous magnesium sulfate. Analysis of the reaction product, using gas chromatographic techniques, indicated 4.7% toluene; 48.3% o-chlorotoluene; and 46.1% p-chlorotoluene. The ratio of o-orthochlorotoluene: p-chlorotoluene (after correction for 1.7% o-chlorotoluene and 0.2% p-chlorotoluene, present in the initial mixture) was 1.03.

EXAMPLE 7

Toluene was chlorinated in a manner substantially similar to that described in Example 6 except that the reaction temperature and catalyst mixture were varied as shown in Table 2, below.

TABLE 2

| Example No. | Catalyst Mixture | Reaction Temperature (°C.) | Product Toluene (%) | O-chloro-toluene (%) | P-chloro-toluene (%) | Benzylic Chlorides (%) | Dichloro-toluene (%) | Ratio of o-chloro-toluene: p-chloro-toluene |
|---|---|---|---|---|---|---|---|---|
| 6 | Ex. 1 | | | | | | | |
| 7 | Ex. 2 | 50 | 3.36 | 46.98 | 48.05 | — | 1.62 | 0.94 |
| 8 | Ex. 2* | 0 | 6.28 | 43.13 | 48.78 | 0.6 | 1.21 | 0.85 |
| 9 | Ex. 3 | 50 | 26.30 | 35.50 | 37.16 | 0.03 | 1.01 | 0.92 |
| 10 | Ex. 3* | 0 | 41.56 | 26.14 | 30.93 | — | 1.37 | 0.80 |
| 11 | Ex. 4* | 50 | 4.70 | 43.95 | 49.29 | 0.22 | 1.86 | 0.89 |
| 12 | Ex. 4* | 0 | 9.70 | 39.13 | 50.16 | — | 1.01 | 0.78 |
| 13 | Ex. 5 | 50 | 2.10 | 45.17 | 49.96 | 0.29 | 2.49 | 0.90 |

TABLE 2-continued

| Example No. | Catalyst Mixture | Reaction Temperature (°C.) | Product | | | Benzylic Chlorides (%) | Dichloro-toluene (%) | Ratio of o-chloro-toluene: p-chloro-toluene |
| --- | --- | --- | --- | --- | --- | --- | --- | --- |
| | | | Toluene (%) | O-chloro-toluene (%) | P-chloro-toluene (%) | | | |
| 14 | Ex. 5* | 0 | 4.49 | 40.78 | 53.58 | — | 1.15 | 0.76 |

*4 parts by weight of iron metal was added as a co-catalyst to the reaction mixture together with the catalyst mixture.

What is claimed is:

1. A process for the directed nuclear chlorination of alkylbenzenes which comprises reacting an alkylbenzene with chlorine in the presence of a catalyst mixture previously prepared by the steps of (a) reacting sulfur monochloride with toluene or chlorotoluene in the presence of a ferric chloride catalyst; and (b) reacting the reaction product of step (a) with chlorine.

2. A process according to claim 1 which comprises reacting an alkylbenzene with chlorine in the presence of a catalyst mixture previously prepared by the step of (a) reacting sulfur monochloride with monochlorotoluene in the presence of a ferric chloride catalyst, and (b) reacting the reaction product of step (a) with chlorine.

3. A process according to claim 2 wherein said alkylbenzene is a benzene compound having one or two alkyl groups substituents on the nucleus thereof, each alkyl group being of one to four carbon atoms.

4. A process according to claim 2 wherein the alkylbenzene is toluene.

5. A process according to claim 4 which comprises reacting toluene with chlorine in the presence of a catalyst mixture previously prepared by the steps of (a) reacting sulfur monochloride with orthochlorotoluene in the presence of ferric chloride and (b) reacting the reaction product of step (a) with chlorine.

6. A process according to claim 5 wherein the catalyst mixture is present in an amount of about 0.1 to about 10 percent by weight based on the weight of toluene.

7. A process according to claim 6 wherein the catalyst mixture is previously prepared by the steps of (a) reacting orthochlorotoluene at a temperature of about 0° to about 80° Celsius in the presence of ferric chloride, the weight ratio of orthochlorotoluene: sulfur monochloride present being about 100:1 to about 0.1:1 and the weight ration of sulfur monochloride: ferric chloride present being about 50:1 to about 5:1; and (b) reacting the reaction product of step (a) with chlorine at a temperature of about 40° to about 80° Celsius.

8. A process according to claim 2 wherein the reaction product of step (a) is diluted by addition of about 25 to about 200 percent by weight of orthochlorotoluene based on the weight of said reaction product, prior to step (b).

9. A process according to claim 8 wherein step (b) is carried out by reacting the reaction product of step (a) with about 10 to about 100 parts of chlorine per 100 parts of reaction product.

10. A process according to claim 8 wherein toluene is reacted with chlorine at a temperature of about −20° to about 110° Celsius in the presence of said previously prepared catalyst mixture.

11. A process according to claim 10 wherein iron metal is present as a co-catalyst.

* * * * *